United States Patent
Abraham et al.

(10) Patent No.: US 12,097,149 B2
(45) Date of Patent: Sep. 24, 2024

(54) COMPENSATING FOR DISTORTION OF IMAGES OF AN EYE FOR A SURGICAL PROCEDURE

(71) Applicant: Alcon Inc., Fribourg (CH)

(72) Inventors: Mario Abraham, Burgthann (DE); Michael Wittnebel, Hirschaid (DE); Friederike Rubin-Schwarz, Nuremberg (DE); Evi Goos, Heroldsbach (DE)

(73) Assignee: ALCON INC., Fribourg (CH)

( * ) Notice: Subject to any disclaimer, the term of this patent is extended or adjusted under 35 U.S.C. 154(b) by 468 days.

(21) Appl. No.: 17/643,456

(22) Filed: Dec. 9, 2021

(65) Prior Publication Data
US 2022/0183888 A1 Jun. 16, 2022

Related U.S. Application Data

(60) Provisional application No. 63/126,293, filed on Dec. 16, 2020.

(51) Int. Cl.
*A61F 9/008* (2006.01)
*A61B 3/00* (2006.01)
*A61B 3/11* (2006.01)

(52) U.S. Cl.
CPC ........ *A61F 9/00838* (2013.01); *A61B 3/0025* (2013.01); *A61B 3/112* (2013.01); *A61F 2009/00872* (2013.01); *A61F 2009/00876* (2013.01)

(58) Field of Classification Search
CPC ........ A61F 9/00838; A61F 2009/00872; A61F 2009/00876; A61F 9/00827; A61B 3/0025; A61B 3/112
See application file for complete search history.

(56) References Cited

U.S. PATENT DOCUMENTS

| | | |
|---|---|---|
| 2016/0150952 A1 | 6/2016 | Raymond et al. |
| 2017/0189233 A1 | 7/2017 | Dewey et al. |
| 2018/0008461 A1 | 1/2018 | Fu et al. |
| 2019/0388270 A1 | 12/2019 | Malek Tabrizi et al. |

FOREIGN PATENT DOCUMENTS

| WO | 2016061454 A1 | 4/2016 |
|---|---|---|

OTHER PUBLICATIONS

Arbelaez et al, "Clinical Outcomes of Corneal Vertex Versus Central Pupil References with Aberration-Free Ablation Strategies and LASIK," Inv. Ophthal. & Vis. Science, Dec. 2008 vol. 49, NR. 12; pp. 5287-5294. ISSN: 1552-5783.

*Primary Examiner* — Scott M. Getzow

(57) ABSTRACT

In certain embodiments, an ophthalmic surgical system for adjusting a dimension of an eye includes a camera and a computer. The camera generates a surgical image of the eye in contact with a patient interface, which distorts the cornea. The surgical image includes the pupil with a real pupil diameter. The computer accesses a diagnostic image of the eye with the cornea having a natural curvature. The natural curvature affects the real pupil diameter to yield a diagnostic pupil diameter of the diagnostic image that is different from the real pupil diameter of the surgical image. The computer adjusts the real pupil diameter of the surgical image using an eye model to yield a refracted pupil diameter that takes into account the curvature of the cornea and uses the refracted pupil diameter to compensate for the difference between the diagnostic and real pupil diameters.

20 Claims, 5 Drawing Sheets

COMPENSATING FOR DISTORTION OF IMAGES OF AN EYE FOR A SURGICAL PROCEDURE

TECHNICAL FIELD

The present disclosure relates generally to ophthalmic surgical systems, and more particularly to compensating for distortion of images of an eye for a surgical procedure.

BACKGROUND

Ophthalmic laser surgical systems generate a pulsed laser beam to perform a surgical procedure on an eye. In some procedures, the laser beam creates photodisruptions at specific points in the eye according to a laser focal spot pattern. The eye should be stabilized throughout the procedure so the laser beam can create photodisruptions that precisely match the pattern.

A patient interface (PI) is usually used to hold the eye in position during the procedure. The patient interface is typically affixed to the eye by a vacuum to secure the eye in place to allow the laser beam to operate on the surgical site during the procedure. Certain patient interfaces change the shape of the cornea. For example, a patient interface may apply pressure to the cornea that may even substantially flatten the cornea. Changing the shape of the cornea typically changes the refractive properties of the cornea.

BRIEF SUMMARY

In certain embodiments, an ophthalmic surgical system for adjusting a dimension of an eye includes a camera and a computer. The camera generates a surgical image of the eye in contact with a patient interface. The eye has a cornea and an iris defining a pupil with a real pupil diameter. The cornea is distorted by the patient interface. The surgical image includes the pupil with the real pupil diameter. The computer: accesses the surgical image of the eye with the distorted cornea; accesses a diagnostic image of the eye with the cornea having a natural curvature, the natural curvature affecting the real pupil diameter to yield a diagnostic pupil diameter of the diagnostic image that is different from the real pupil diameter of the surgical image; adjusts the real pupil diameter of the surgical image using an eye model to yield a refracted pupil diameter that takes into account the curvature of the cornea; and uses the refracted pupil diameter to compensate for a difference between the diagnostic pupil diameter of the diagnostic image and the real pupil diameter of the surgical image.

Embodiments may have none, one, two or more, or all of the following features: The ophthalmic surgical system further comprises a laser device that directs a laser beam towards the eye. The computer further uses the refracted pupil diameter to perform a surgical procedure on the eye to compensate for difference between the diagnostic pupil diameter of the diagnostic image and the real pupil diameter of the surgical image. Adjusting the real pupil diameter of the surgical image using the eye model comprises: accessing information describing one or more of the following of the eye: a distance between structures of the eye, a refractive power of a structure of the eye, a thickness of a structure of the eye, and a curvature of a structure of the eye; and including the information in the eye model. Using the refracted pupil diameter to compensate for the difference comprises: aligning the surgical image with the diagnostic image according to the refracted pupil diameter. Using the refracted pupil diameter to compensate for the difference comprises: determining a pupil centroid shift according to the refracted pupil diameter; and determining a pupil center according to the pupil centroid shift. The computer further: adjusts a dimension of the iris of the surgical image using the eye model; and corrects for torsion according to the adjusted iris dimension. The computer may adjust the dimension of the iris of the surgical image by: determining an imaging ratio of the real pupil diameter to the refracted pupil diameter; and adjusting the dimension of the iris according to the imaging ratio. The computer may correct for torsion according to the adjusted iris structure by: identifying a pseudo-rotation of the iris according to the dimension of the iris; and taking the pseudo-rotation into account to correct for torsion. The cornea may have a decreased curvature or may be substantially flattened.

In certain embodiments, an ophthalmic surgical system for adjusting a dimension of an eye includes a camera and a computer. The camera generates a surgical image of the eye in contact with a patient interface. The eye has a cornea and an iris defining a pupil with a real pupil diameter. The cornea is distorted by the patient interface. The surgical image includes the pupil with an interface pupil diameter. The computer: accesses the surgical image of the eye with the distorted cornea; accesses a diagnostic image of the eye with the cornea having a natural curvature, the natural curvature affecting the real pupil diameter to yield a diagnostic pupil diameter of the diagnostic image that is different from the interface pupil diameter of the surgical image; adjusts the interface pupil diameter of the surgical image using an eye model to yield a refracted pupil diameter that takes into account the curvature of the cornea; and uses the refracted pupil diameter to compensate for a difference between the diagnostic pupil diameter of the diagnostic image and the interface pupil diameter of the surgical image.

Embodiments may have none, one, two or more, or all of the following features: The ophthalmic surgical system further comprises a laser device configured to direct a laser beam towards the eye. The computer further uses the refracted pupil diameter to perform a surgical procedure on the eye to compensate for difference between the diagnostic pupil diameter of the diagnostic image and the interface pupil diameter of the surgical image. Adjusting the interface pupil diameter of the surgical image using the eye model comprises: accessing information describing one or more of the following of the eye: a distance between structures of the eye, a refractive power of a structure of the eye, a thickness of a structure of the eye, and a curvature of a structure of the eye; and including the information in the eye model. Using the refracted pupil diameter to compensate for the difference comprises: aligning the surgical image with the diagnostic image according to the refracted pupil diameter. Using the refracted pupil diameter to compensate for the difference comprises: determining a pupil centroid shift according to the refracted pupil diameter; and determining a pupil center according to the pupil centroid shift. The computer further: adjusts a dimension of the iris of the surgical image using the eye model; and corrects for torsion according to the adjusted iris dimension. The computer may adjust the dimension of the iris of the surgical image by: determining an imaging ratio of the interface pupil diameter to the refracted pupil diameter; and adjusting the dimension of the iris according to the imaging ratio. The computer may correct for torsion according to the adjusted iris structure by: identifying a pseudo-rotation of the iris according to the dimension of the iris; and taking the pseudo-rotation into account to correct for torsion.

In certain embodiments, an ophthalmic surgical system for adjusting a dimension of an eye includes a camera, a laser device, and a computer. The camera generates a surgical image of the eye in contact with a patient interface. The eye has a cornea and an iris defining a pupil with a real pupil diameter. The cornea is distorted by the patient interface. The surgical image includes the pupil with the real pupil diameter. The laser device directs a laser beam towards the eye. The computer accesses the surgical image of the eye with the distorted cornea, and accesses a diagnostic image of the eye with the cornea having a natural curvature. The natural curvature affects the real pupil diameter to yield a diagnostic pupil diameter of the diagnostic image that is different from the real pupil diameter of the surgical image. The computer adjusts the real pupil diameter of the surgical image using an eye model to yield a refracted pupil diameter that takes into account the curvature of the cornea, where adjusting the real pupil diameter of the surgical image using the eye model comprises: accessing information describing one or more of the following of the eye: a distance between structures of the eye, a refractive power of a structure of the eye, a thickness of a structure of the eye, and a curvature of a structure of the eye; and including the information in the eye model. The computer adjusts a dimension of the iris of the surgical image using the eye model and corrects for torsion according to the adjusted iris dimension, where adjusting the iris structure of the surgical image comprises: determining an imaging ratio of the real pupil diameter to the refracted pupil diameter; and adjusting the dimension of the iris according to the imaging ratio, and where correcting for torsion according to the adjusted iris structure comprises: identifying a pseudo-rotation of the iris according to the dimension of the iris; and taking the pseudo-rotation into account to correct for torsion. The computer uses the refracted pupil diameter to compensate for a difference between the diagnostic pupil diameter of the diagnostic image and the real pupil diameter of the surgical image, where using the refracted pupil diameter to compensate for the difference comprises: determining a pupil centroid shift according to the refracted pupil diameter; and determining a pupil center according to the pupil centroid shift; and aligning the surgical image with the diagnostic image according to the refracted pupil diameter. The computer uses the refracted pupil diameter to perform a surgical procedure on the eye to compensate for difference between the diagnostic pupil diameter of the diagnostic image and the real pupil diameter of the surgical image.

Embodiments may or may not have the following feature: The cornea may have a decreased curvature or be substantially flattened.

DESCRIPTION OF EXAMPLE EMBODIMENTS

Figure 1:
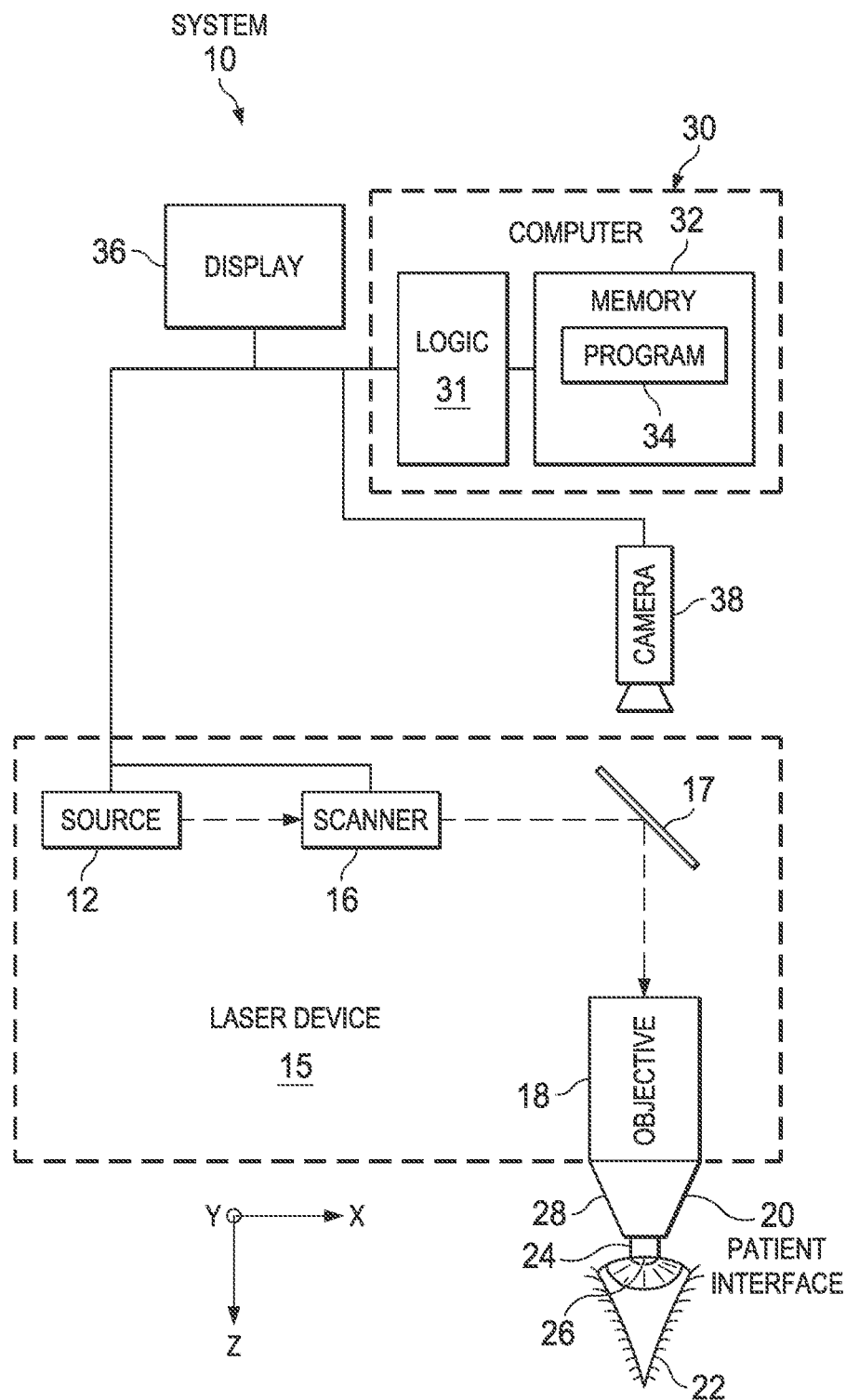
FIG. 1 illustrates an example of an ophthalmic surgical system configured to compensate for distortion of images of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Diagnostic measurements of the eye may be performed when the cornea is in its natural curved state. This curvature refracts light reflected from eye structures (e.g., the pupil and iris), such that the structures may appear larger. During surgery, certain patient interfaces flatten the cornea, such that the corneal surface does not affect the size of the structures. Accordingly, there may be differences between diagnostic and surgical images. To compensate for the differences, an eye model is used to adjust dimensions of the eye structures of the surgical image to correspond with the eye structures of the diagnostic image.

FIG. 1 illustrates an example of an ophthalmic surgical system 10 configured to compensate for distortion of images of an eye, according to certain embodiments. In the embodiments, a computer uses an eye model to compensate for differences between a diagnostic pupil diameter of a diagnostic image and a real pupil diameter of a surgical image. A surgical image is taken when the cornea is substantially flattened by a patient interface. The flattened cornea generally does not affect the imaging of the real pupil diameter. A diagnostic image is taken when the cornea has its natural curvature. The curvature affects the real pupil diameter to yield a diagnostic pupil diameter that is different from the real pupil diameter. The computer uses an eye model to adjust the real pupil diameter of the surgical image to yield a refracted pupil diameter that takes into account the curvature of the cornea. The computer then uses the refracted pupil diameter of the surgical image to perform the surgical procedure on the eye to compensate for the difference between the diagnostic pupil diameter and the real pupil diameter.

In the illustrated example, ophthalmic surgical system 10 includes a laser device 15, a patient interface 20, a camera 38, and a control computer 30, coupled as shown. Laser device 15 includes controllable components, such as a laser source 12, a scanner 16, one or more optical elements 17, and/or a focusing objective 18, controllable by a computer such as computer 30, coupled as shown. Patient interface 20 includes a contact portion 24 (with an abutment face 26) and a sleeve 28 coupled as shown. Computer 30 includes logic 31, a memory 32 (which stores a computer program 34), and a display 36, coupled as shown.

Ophthalmic surgical system 10 may perform any suitable surgical procedure, such as corneal refractive or laser coagulation surgery. The surgical procedure may have an associated laser focal spot pattern that describes the target locations of the laser pulses in the cornea. Certain types of procedures, e.g., lenticule extraction, require precise placement of the laser pulses according to the laser focal spot pattern, which in turn requires precise alignment of surgical and diagnostic images.

Turning to the parts of system 10, as an example overview of laser device 15, laser source 12 generates a laser beam having ultrashort pulses, where a propagation direction of the laser beam defines a z-axis and/or z-direction. Scanner 16 directs a focal point of the laser beam in an xy-plane that is orthogonal to the z-axis. Objective 18 focuses the focal point towards the cornea of eye 22.

In certain embodiments, laser source 12 generates a laser beam with ultrashort pulses. An ultrashort pulse refers to a light pulse that has a duration that is less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 longitudinally and transversely directs the focal point of the laser beam. The longitudinal direction refers to the direction of the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the focal point. The transverse direction refers to directions orthogonal to the direction of beam propagation, i.e., the x- and y-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 interfaces with the cornea of eye 22 to couple eye 22 to laser device 15. In the example, patient interface 20 has sleeve 28 coupled to contact portion 24. Sleeve 28 detachably couples to focusing objective 18. Contact portion 24 may be translucent or transparent to the laser beam and has an abutment face 26 that interfaces with the cornea. Abutment face 26 may have any suitable shape, e.g., planar, convex, or concave.

Camera 38 records surgical images of eye 22 in real time during a surgical procedure. Examples of camera 38 include a video, optical coherence tomography (OCT), or eye-tracking camera. Camera 38 delivers image data, which represent recorded surgical images of the eye 22, to computer 30.

Computer 30 controls controllable components (e.g., laser source 12, scanner 16, optical elements 17, and/or focusing objective 18) in accordance with instructions (which may be stored in computer program 34) to photodisrupt corneal tissue. Memory 32 stores information that can be accessed by computer 30. Examples of information include: images (e.g., surgical and/or diagnostic images), an eye model, information describing a particular eye, information describing pupil centroid shifts, and other suitable information.

In certain embodiments, computer 30 uses an eye model to compensate for differences between a diagnostic pupil diameter of a diagnostic image and a real pupil diameter of a surgical image. In the embodiments, computer 30 accesses the surgical image and diagnostic image of the eye and uses an eye model to adjust the real pupil diameter of the surgical image to yield a refracted pupil diameter that takes into account the curvature of the cornea. For example, computer 30 determines how the eye model predicts the natural curvature of the cornea affects the real pupil diameter $PD_{real}$ to determine the refracted pupil diameter $PD_{refracted}$. Computer 30 then uses the refracted pupil diameter to perform the surgical procedure on the eye to compensate for difference between the diagnostic pupil diameter and the real pupil diameter.

Computer 30 may use the refracted pupil diameter to perform the surgical procedure in any suitable manner, such as aligning surgical and diagnostic images according to the refracted pupil diameter. In certain embodiments, computer 30 uses the refracted pupil diameter to compensate for pupil centroid shift. Pupil centroid shift occurs when the pupil center moves as the pupil diameter changes. In the embodiments, computer 30 determines the pupil centroid shift according to the refracted pupil diameter of the surgical image, and determines the pupil center according to the pupil centroid shift and the refracted pupil diameter of the surgical image. For example, computer 30 accesses a table of pupil diameters and associated pupil centroid shifts to determine the centroid shift associated with the refractive pupil diameter. Computer 30 then applies the centroid shift to determine the pupil center.

In certain embodiments, computer 30 uses the eye model to correct for torsion. Torsion refers to twisting of the eye, which may occur when the patient moves from a seated to a lying position. An asymmetric eye structure, such as the iris, can be used to correct torsion. In the embodiments, computer 30 uses the eye model to adjust a dimension of the iris of the surgical image and then corrects for torsion according to the adjusted iris dimension. Computer 30 may use the eye model to adjust the iris dimension of the surgical image by: determining an imaging ratio of the real pupil diameter to the refracted pupil diameter; and adjusting the iris dimension according to the imaging ratio. This is described in more detail with reference to FIGS. 4A through 4C.

Computer 30 may take into account pseudo-rotation, which is an apparent rotation which arises from the change in pupil size and hence a shift in the structures of the iris, but which does not imply a real torsion of the eye. In the embodiments, computer 30 corrects for torsion according to the adjusted iris structure by: identifying a pseudo-rotation of the iris structure according to the adjusted iris structure; and taking the pseudo-rotation into account to correct for torsion. For example, computer 30 accesses a table of pupil diameters and associated pseudo-rotations to determine the pseudo-rotation associated with the refractive pupil diameter. This is described in more detail with reference to FIGS. 4A through 4C.

Figure 2A:
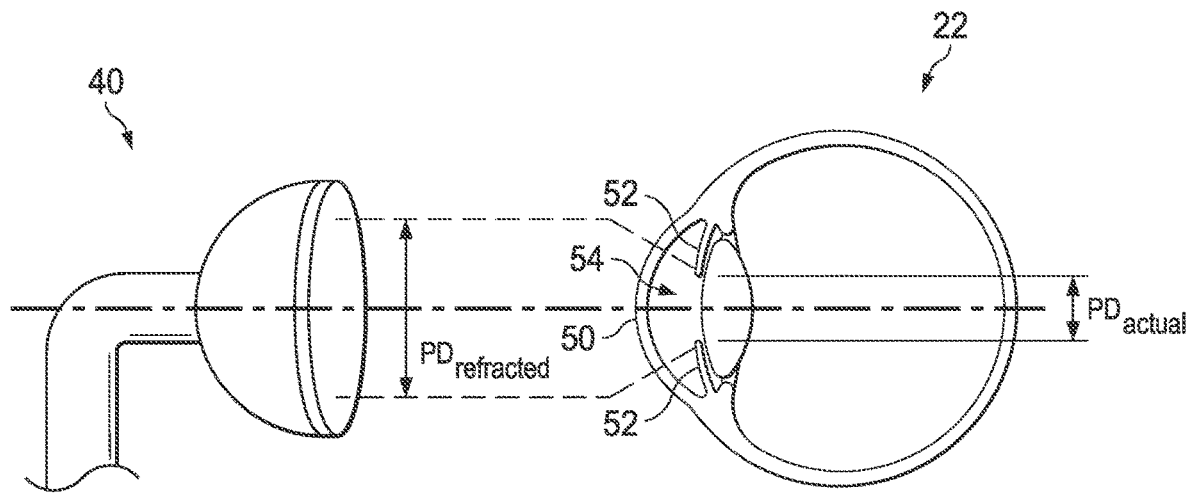
FIGS. 2A and 2B illustrate how the curvature of the cornea affects the pupil diameter in a diagnostic image.
Figure 2B:
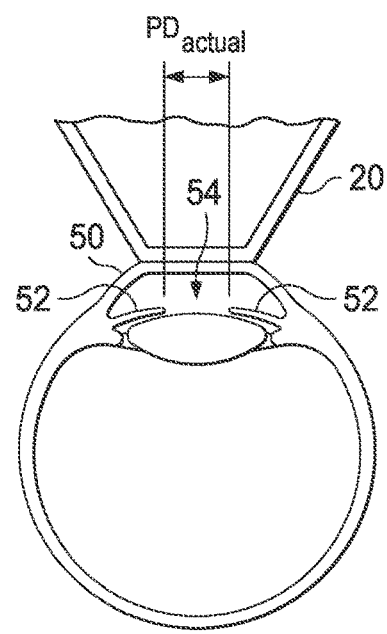

FIGS. 2A and 2B illustrate how the curvature of the cornea affects the pupil diameter in a diagnostic image. FIG. 2A shows a diagnostic device 40 measuring eye 22, which includes a cornea 50 and an iris 52 that defines a pupil 54 having a pupil diameter PD. Diagnostic device 40 generates an image of eye 22, typically without contact with cornea 50 or without changing the shape of cornea 50. Ophthalmic surgical system 10 may use the diagnostic image to treat eye 22. For example, the diagnostic image or a treatment pattern based on the diagnostic image may be aligned with a surgical image of eye 22.

In the illustrated example, pupil 54 has a real pupil diameter $PD_{real}$. The curvature of cornea 50 refracts light reflected from eye structures, such as iris 52 and pupil 54, which changes the imaging ratios. As a result, a diagnostic image of an eye structure has refracted dimensions that are larger than the real dimensions. For example, pupil 54 has a refracted pupil diameter $PD_{refracted}$ that is larger than real pupil diameter $PD_{real}$. Similarly, iris 52 has a refracted diameter that is larger than the real diameter.

FIG. 2B shows patient interface 20 of ophthalmic surgical system 10 applanating eye 22. A patient interface 20 may distort the shape of the cornea such that the distortion affects the dimensions of structures of eye 22. In the illustrated example, patent interface 20 flattens cornea 50 such that cornea 50 does not refract light reflected from eye structures. As a result, a surgical image of an eye structure has dimensions that are substantially the same as the real dimensions. For example, pupil 54 has a pupil diameter that is substantially the same size as real pupil diameter $PD_{real}$. In other examples, patient interface 20 may decrease the curvature of the surface of the cornea, but not flatten the surface, such that the pupil has an interface pupil diameter that is closer to, but not the same size as, real pupil diameter $PD_{real}$.

Figure 3A:
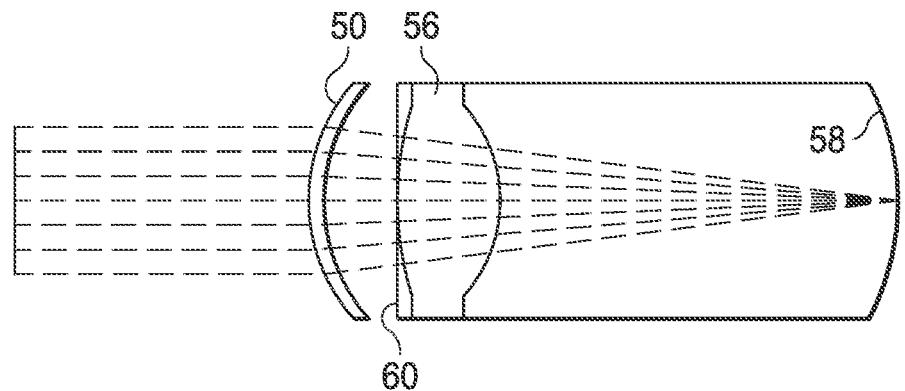
FIGS. 3A and 3B illustrate an example of eye models describing diagnostic and surgical imaging of an eye.
Figure 3B:
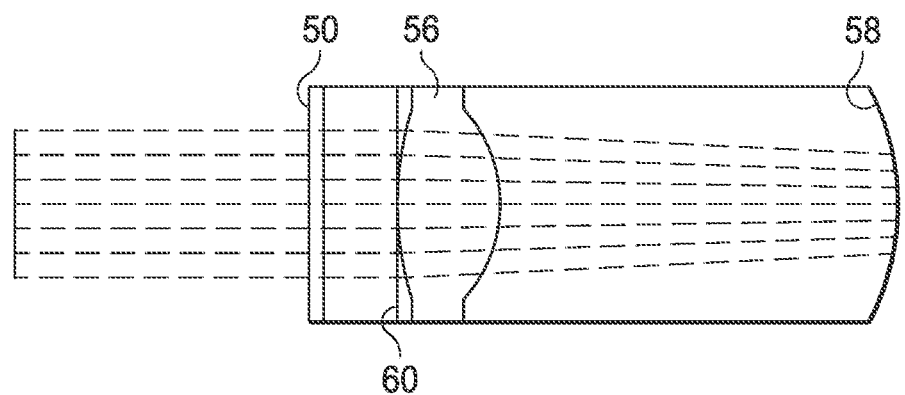

FIGS. 3A and 3B illustrate an example of eye models describing diagnostic and surgical imaging of an eye. An eye model uses geometric optics to describe the paths of light rays through an eye. Any suitable eye model may be used, e.g., a standardized eye model, such as the Navarro model.

Computer 30 may use an eye model to adjust the real pupil diameter in any suitable manner. For example, computer 30 may use an eye model to determine the refracted pupil diameter $PD_{refracted}$ that corresponds to a given real pupil diameter $PD_{real}$ and/or to determine the real pupil diameter $PD_{real}$ that corresponds to a given refracted pupil diameter $PD_{refracted}$. In certain embodiments, computer 30 determines how the eye model predicts the natural curvature of the cornea affects the real pupil diameter $PD_{real}$ to determine the refracted pupil diameter $PD_{refracted}$. In certain embodiments, computer 30 determines how the eye model predicts a decreased curvature of the cornea (resulting from a patient interface 20) affects the real pupil diameter $PD_{real}$ to determine an interface pupil diameter $PD_{interface}$. In the embodiments, computer 30 may use this information to determine a relationship between the interface pupil diameter $PD_{interface}$ and the refracted pupil diameter $PD_{refracted}$.

In certain embodiments, computer 30 may customize an eye model with information (e.g., measurements) describing a specific eye 22. For example, the information may describe one or more of the following: the distance between structures of an eye (e.g., the anterior chamber depth and/or eye length); the refractive power of a structure (e.g., the refractive power of the cornea and/or lens), the thickness of a structure (e.g., the lens thickness); and/or the curvature of a structure (e.g., the curvature of the cornea, lens, and/or retina). The information may describe the eye with the cornea having its natural curvature, a distorted curvature, or substantially flattened.

In the example, model shows an eye with cornea 50, lens 56, and retina 58. A pupil plane 60 is the plane at which pupil 54 is located. FIG. 3A shows an eye model with a cornea 50 having a curvature. The curvature of cornea 50 generally focuses incoming light rays through lens 56 and onto retina 58, i.e., the light rays substantially converge to meet at retina 58. In doing so, the light rays converge slightly at pupil plane 60. Accordingly, light reflected from eye structures at pupil plane 60 is refracted by cornea 50, yielding a refracted pupil diameter $PD_{refracted}$ that is larger than real pupil diameter $PD_{real}$.

FIG. 3B shows an eye model with a flattened cornea 50. The flattened cornea 50 does not refractively affect the light rays. Lens 56 refracts the light rays slightly, but this occurs between the pupil plane 60 and retina 58. Accordingly, the pupil diameter is substantially the same as real pupil diameter $PD_{real}$. In other examples, patient interface 20 may decrease the curvature of the surface of the cornea, but not flatten the surface, such that the pupil has an interface pupil diameter that is closer to, but not the same size as, real pupil diameter $PD_{real}$.

Figure 4A:
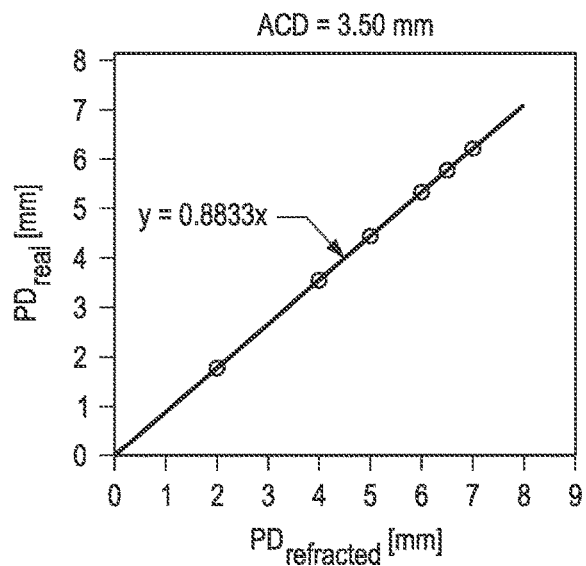
FIGS. 4A, 4B, and 4C illustrate the linear relationship between real pupil diameter $PD_{real}$ and refracted pupil diameter $PD_{refracted}$ at different anterior chamber depths (ACDs)
Figure 4B:
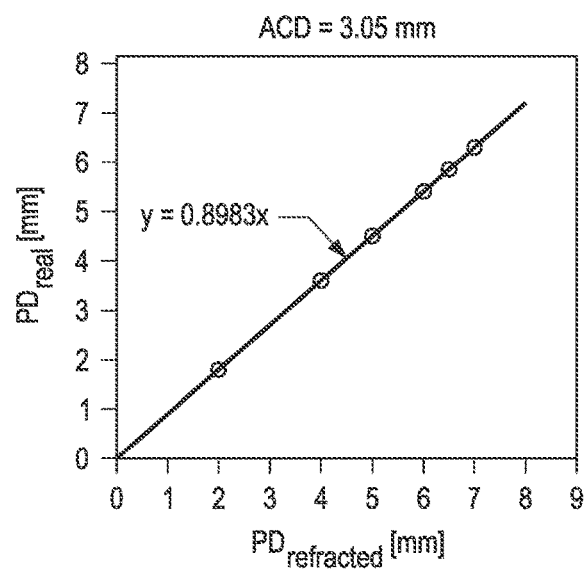
Figure 4C:
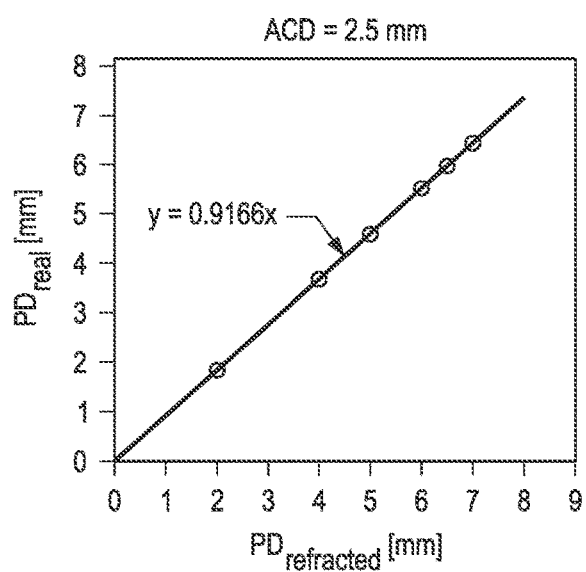

FIGS. 4A, 4B, and 4C illustrate the linear relationship between real pupil diameter $PD_{real}$ and refracted pupil diameter $PD_{refracted}$ at different anterior chamber depths (ACDs). The ratio $PD_{real}/PD_{refracted}$ is an imaging ratio that provides an estimate of a refracted dimension, given a real dimension, or vice-versa. For example, given real dimension $D_{real}$, refracted dimension $D_{refracted}$ may be calculated as $D_{refracted}=PD_{refracted}/PD_{real} \times D_{real}$. Given refracted dimension $D_{refracted}$, real dimension $D_{real}$ may be calculated as $D_{real}=PD_{real}/PD_{refracted} \times D_{refracted}$.

In certain embodiments, computer 30 uses imaging ratio $PD_{real}/PD_{refracted}$ to correct for torsion. In the embodiments, computer 30 adjusts a real dimension of an iris in a surgical image according to imaging ratio $PD_{real}/PD_{refracted}$ to yield a refracted iris dimension. Computer 30 then uses the refracted iris dimension to correct for torsion to align the surgical image with a diagnostic image. In certain embodiments, computer 30 may take into account pseudo-rotation. In the embodiments, computer 30 identifies a pseudo-rotation of the iris structure using the refracted iris dimension. Computer 30 then does not treat the pseudo-rotation as a real rotation in correcting for torsion.

As patient interface 20 applanates eye 22, interface 20 presses on cornea 50, decreasing the anterior chamber depth. The imaging ratio $PD_{real}/PD_{refracted}$ varies with the anterior chamber depth. FIG. 4A shows the linear relationship at an ACD of 3.50 millimeters (mm), where $PD_{real}/PD_{refracted}$ is 0.8833. FIG. 4B shows the linear relationship at an ACD of 3.05 mm, where $PD_{real}/PD_{refracted}$ is 0.8983. FIG. 4C shows the linear relationship at an ACD of 2.50 mm, where $PD_{real}/PD_{refracted}$ is 0.9166.

Figure 5:
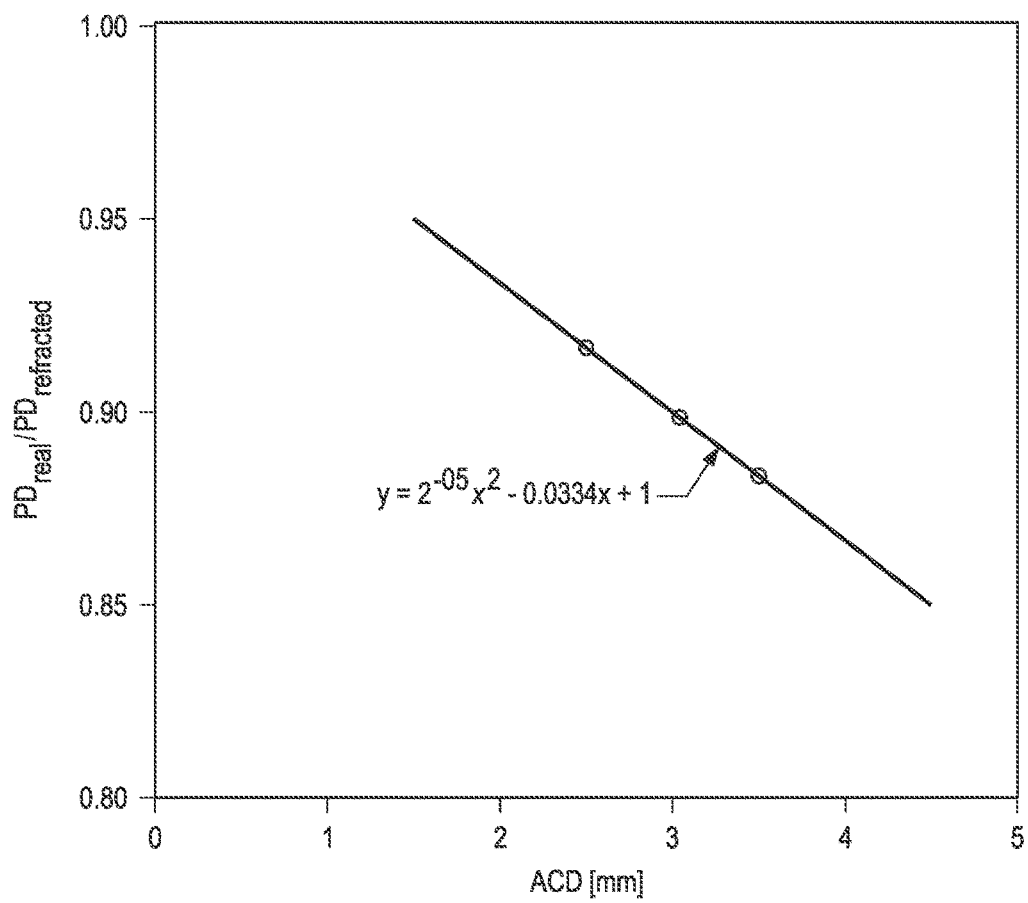
FIG. 5 illustrates a substantial linear relationship between the anterior chamber depth (ACD) and the imaging ratio $PD_{real}/PD_{refracted}$, as described in FIGS. 4A to 4C.

FIG. 5 illustrates a substantial linear relationship between the anterior chamber depth (ACD) and the imaging ratio $PD_{real}/PD_{refracted}$, as described in FIGS. 4A to 4C. FIG. 5 presents a graph 63 that plots the imaging ratios $PD_{real}/PD_{refracted}$ along the y-axis relative to the anterior chamber depths along the x-axis. The relationship may be described by $y=2^{-05}x^2-0.033x+1 \sim 0.0334x+1$. Accordingly, given the anterior chamber depth (of the applanated eye) and real pupil diameter $PD_{real}$, refracted pupil diameter $PD_{refracted}$ can be determined.

Figure 6:
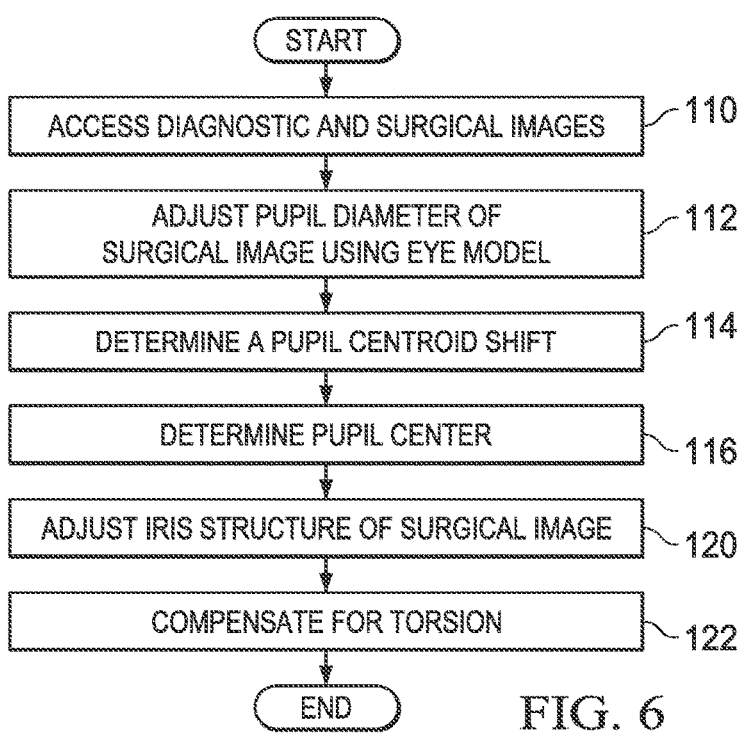
FIG. 6 illustrates an example of a method for compensating for distortion of images of an eye for a surgical procedure, which may be performed by system 10 of FIG. 1.

FIG. 6 illustrates an example of a method for compensating for distortion of images of an eye for a surgical procedure, which may be performed by system 10 of FIG. 1. Certain steps of the method may be performed by computer 30 sending instructions to other components of system 10.

The method starts at step 110, where computer 30 accesses diagnostic and surgical images of the eye. Computer 30 adjusts the pupil diameter of the surgical image using an eye model to yield a refracted pupil diameter at step 112. For example, computer 30 determines how the eye model shows the natural curvature of the cornea affects the real pupil diameter $PD_{real}$ to determine the refracted pupil diameter $PD_{refracted}$.

Computer 30 determines a pupil centroid shift using the refracted pupil diameter at step 114. For example, computer 30 accesses a table of pupil diameters and associated pupil centroid shifts to determine the centroid shift associated with the refractive pupil diameter. Computer 30 determines the pupil center according to the pupil centroid shift at step 116. For example, computer 30 applies the centroid shift to determine the pupil center, i.e., the position of the diagnostic pupil center.

Computer 30 adjusts the iris structure of the surgical image using the refracted pupil diameter at step 120. For example, computer 30 determines imaging ratio $PD_{real}/PD_{refracted}$ and adjusts a real dimension of the iris according to an eye model in a surgical image according to imaging ratio $PD_{real}/PD_{refracted}$ to yield a refracted iris dimension. Computer 30 may also identify a pseudo-rotation of the iris structure using the refracted iris dimension. Computer 30 compensates for torsion using the adjusted iris structure at step 122. For example, computer 30 uses the refracted iris dimension to correct for torsion to align the surgical image with a diagnostic image, but does not treat the pseudo-rotation as a real rotation in correcting for torsion. The method then ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for adjusting a dimension of an eye, comprising:
   a camera configured to generate a surgical image of the eye in contact with a patient interface, the eye having a cornea and an iris defining a pupil, the pupil having a real pupil diameter, the cornea distorted by the patient interface, the surgical image including the pupil with the real pupil diameter; and
   a computer configured to:
      access the surgical image of the eye with the distorted cornea;
      access a diagnostic image of the eye with the cornea having a natural curvature, the natural curvature affecting the real pupil diameter to yield a diagnostic pupil diameter of the diagnostic image that is different from the real pupil diameter of the surgical image;
      adjust the real pupil diameter of the surgical image using an eye model to yield a refracted pupil diameter that takes into account the curvature of the cornea; and
      use the refracted pupil diameter to compensate for a difference between the diagnostic pupil diameter of the diagnostic image and the real pupil diameter of the surgical image.

2. The ophthalmic surgical system of claim 1:
   further comprising a laser device configured to direct a laser beam towards the eye; and
   the computer further configured to:
      use the refracted pupil diameter to perform a surgical procedure on the eye to compensate for difference between the diagnostic pupil diameter of the diagnostic image and the real pupil diameter of the surgical image.

3. The ophthalmic surgical system of claim 1, wherein adjusting the real pupil diameter of the surgical image using the eye model comprises:
   accessing information describing one or more of the following of the eye: a distance between structures of the eye, a refractive power of a structure of the eye, a thickness of a structure of the eye, and a curvature of a structure of the eye; and
   including the information in the eye model.

4. The ophthalmic surgical system of claim 1, wherein using the refracted pupil diameter to compensate for the difference comprises:
aligning the surgical image with the diagnostic image according to the refracted pupil diameter.

5. The ophthalmic surgical system of claim 1, wherein using the refracted pupil diameter to compensate for the difference comprises:
determining a pupil centroid shift according to the refracted pupil diameter; and
determining a pupil center according to the pupil centroid shift.

6. The ophthalmic surgical system of claim 1, the computer further configured to:
adjust a dimension of the iris of the surgical image using the eye model; and
correct for torsion according to the adjusted iris dimension.

7. The ophthalmic surgical system of claim 6, wherein adjusting the dimension of the iris of the surgical image comprises:
determining an imaging ratio of the real pupil diameter to the refracted pupil diameter; and
adjusting the dimension of the iris according to the imaging ratio.

8. The ophthalmic surgical system of claim 6, wherein correcting for torsion according to the adjusted iris structure comprises:
identifying a pseudo-rotation of the iris according to the dimension of the iris; and
taking the pseudo-rotation into account to correct for torsion.

9. The ophthalmic surgical system of claim 1, wherein the cornea has a decreased curvature.

10. The ophthalmic surgical system of claim 1, wherein the cornea is substantially flattened.

11. An ophthalmic surgical system for adjusting a dimension of an eye, comprising:
a camera configured to generate a surgical image of the eye in contact with a patient interface, the eye having a cornea and an iris defining a pupil, the pupil having a real pupil diameter, the cornea distorted by the patient interface, the surgical image including the pupil with an interface pupil diameter; and
a computer configured to:
access the surgical image of the eye with the distorted cornea;
access a diagnostic image of the eye with the cornea having a natural curvature, the natural curvature affecting the real pupil diameter to yield a diagnostic pupil diameter of the diagnostic image that is different from the interface pupil diameter of the surgical image;
adjust the interface pupil diameter of the surgical image using an eye model to yield a refracted pupil diameter that takes into account the curvature of the cornea; and
use the refracted pupil diameter to compensate for a difference between the diagnostic pupil diameter of the diagnostic image and the interface pupil diameter of the surgical image.

12. The ophthalmic surgical system of claim 11:
further comprising a laser device configured to direct a laser beam towards the eye; and
the computer further configured to:
use the refracted pupil diameter to perform a surgical procedure on the eye to compensate for difference between the diagnostic pupil diameter of the diagnostic image and the interface pupil diameter of the surgical image.

13. The ophthalmic surgical system of claim 11, wherein adjusting the interface pupil diameter of the surgical image using the eye model comprises:
accessing information describing one or more of the following of the eye: a distance between structures of the eye, a refractive power of a structure of the eye, a thickness of a structure of the eye, and a curvature of a structure of the eye; and
including the information in the eye model.

14. The ophthalmic surgical system of claim 11, wherein using the refracted pupil diameter to compensate for the difference comprises:
aligning the surgical image with the diagnostic image according to the refracted pupil diameter.

15. The ophthalmic surgical system of claim 11, wherein using the refracted pupil diameter to compensate for the difference comprises:
determining a pupil centroid shift according to the refracted pupil diameter; and
determining a pupil center according to the pupil centroid shift.

16. The ophthalmic surgical system of claim 11, the computer further configured to:
adjust a dimension of the iris of the surgical image using the eye model; and
correct for torsion according to the adjusted iris dimension.

17. The ophthalmic surgical system of claim 16, wherein adjusting the dimension of the iris of the surgical image comprises:
determining an imaging ratio of the interface pupil diameter to the refracted pupil diameter; and
adjusting the dimension of the iris according to the imaging ratio.

18. The ophthalmic surgical system of claim 16, wherein correcting for torsion according to the adjusted iris structure comprises:
identifying a pseudo-rotation of the iris according to the dimension of the iris; and
taking the pseudo-rotation into account to correct for torsion.

19. An ophthalmic surgical system for adjusting a dimension of an eye, comprising:
a camera configured to generate a surgical image of the eye in contact with a patient interface, the eye having a cornea and an iris defining a pupil, the pupil having a real pupil diameter, the cornea distorted by the patient interface, the surgical image including the pupil with the real pupil diameter;
a laser device configured to direct a laser beam towards the eye; and
a computer configured to:
access the surgical image of the eye with the distorted cornea;
access a diagnostic image of the eye with the cornea having a natural curvature, the natural curvature affecting the real pupil diameter to yield a diagnostic pupil diameter of the diagnostic image that is different from the real pupil diameter of the surgical image;
adjust the real pupil diameter of the surgical image using an eye model to yield a refracted pupil diameter that takes into account the curvature of the cornea, adjusting the real pupil diameter of the surgical image using the eye model comprising: accessing information describing one or more of the following of the eye: a distance between structures of the eye, a refractive power of a structure of the eye, a thickness of a structure of the eye, and a curvature of a structure of the eye; and including the information in the eye model;

adjust a dimension of the iris of the surgical image using the eye model and correct for torsion according to the adjusted iris dimension, adjusting the iris structure of the surgical image comprising: determining an imaging ratio of the real pupil diameter to the refracted pupil diameter; and adjusting the dimension of the iris according to the imaging ratio, correcting for torsion according to the adjusted iris structure comprising: identifying a pseudo-rotation of the iris according to the dimension of the iris; and taking the pseudo-rotation into account to correct for torsion;

use the refracted pupil diameter to compensate for a difference between the diagnostic pupil diameter of the diagnostic image and the real pupil diameter of the surgical image, using the refracted pupil diameter to compensate for the difference comprising:
determining a pupil centroid shift according to the refracted pupil diameter; and determining a pupil center according to the pupil centroid shift; and
aligning the surgical image with the diagnostic image according to the refracted pupil diameter; and use the refracted pupil diameter to perform a surgical procedure on the eye to compensate for difference between the diagnostic pupil diameter of the diagnostic image and the real pupil diameter of the surgical image.

20. The ophthalmic surgical system of claim 19, wherein the cornea is substantially flattened.

* * * * *